(12) United States Patent
Pages

(10) Patent No.: US 6,267,925 B1
(45) Date of Patent: Jul. 31, 2001

(54) METHOD FOR CRYOPRESERVATION AND RECOVERY OF RED BLOOD CELLS

(75) Inventor: Etienne Pages, Segny (FR)

(73) Assignee: Haemonetics Corporation, Braintree, MA (US)

( * ) Notice: Subject to any disclaimer, the term of this patent is extended or adjusted under 35 U.S.C. 154(b) by 0 days.

(21) Appl. No.: 09/206,916

(22) Filed: Dec. 7, 1998

(51) Int. Cl.$^7$ .................................................. A61K 35/18
(52) U.S. Cl. ........................... 422/41; 422/3; 422/101; 604/6.01; 604/6.02; 435/2; 435/3; 424/529; 424/533; 210/739; 210/741; 210/749; 210/767; 210/772; 62/64
(58) Field of Search ................. 435/2, 3; 604/6.01, 604/6.02; 424/529, 533; 422/41, 3, 101; 210/767, 416.1, 739, 749, 772, 741; 62/64

(56) References Cited

U.S. PATENT DOCUMENTS

| | | | |
|---|---|---|---|
| Re. 33,924 | 5/1992 | Valeri | 604/6 |
| 3,145,713 | 8/1964 | Latham, Jr. . | |
| 4,030,314 | 6/1977 | Strehler et al. | 62/54 |
| 4,478,824 | 10/1984 | Franco et al. . | |
| 4,585,735 | 4/1986 | Meryman et al. | 435/2 |
| 4,774,088 | 9/1988 | Vora | 435/2 |
| 4,812,310 | 3/1989 | Sato et al. | 435/2 |
| 4,931,276 | 6/1990 | Franco et al. | 424/533 |
| 5,242,792 | 9/1993 | Rudolph et al. | 435/2 |
| 5,250,303 | 10/1993 | Meryman et al. | 424/533 |
| 5,487,971 | 1/1996 | Holme et al. | 435/2 |
| 5,580,714 | 12/1996 | Polovina | 435/2 |
| 5,601,972 | 2/1997 | Meryman | 435/2 |

FOREIGN PATENT DOCUMENTS

| | | |
|---|---|---|
| 2259878 | 7/1999 | (CA) . |
| WO95/32624 | 12/1995 | (WO) . |
| WO99/08513 | 2/1999 | (WO) . |

OTHER PUBLICATIONS

C. R. Valeri; Preservation of Red Blood Cells and Platelets: Freezing, Storage, Recovery, and Quality; © 1991 Wiley–Liss, Inc.

*Primary Examiner*—David A. Reifsnyder
(74) *Attorney, Agent, or Firm*—Cesari and McKenna, LLP

(57) ABSTRACT

A system dynamically adjusts the delivery rate of a cryopreservation solution to red blood cells to permit freezing. The delivery rate is preferably determined according to an equation that maintains a linear change of red blood cell osmolarity over time so as to prevent osmolarity shock of the red blood cells. In the preferred embodiment, the system includes a controller that is preconfigured to automatically deliver the cryopreservation solution to the red blood cells in accordance with the equation. The system may also support the recovery of thawed red blood cells by diluting the red blood cells and washing them of the cryopreservative. Again, the system preferably adjusts the delivery rate of a dilution solution so as to prevent osmolarity shock of the red blood cells during the recovery phase. The recovered red blood cells may be suspended in a preservation solution to further increase their shelf-life following the recovery phase.

24 Claims, 8 Drawing Sheets

METHOD FOR CRYOPRESERVATION AND RECOVERY OF RED BLOOD CELLS

FIELD OF THE INVENTION

The present invention relates generally to the storage of blood and blood components, and more specifically, to an improved system for adding a cryopreservation solution to red blood cells prior to freezing and for washing that solution from the red blood cells prior to their use.

BACKGROUND OF THE INVENTION

Human blood predominantly includes three types of specialized cells: red blood cells, white blood cells, and platelets. These cells are suspended in a complex aqueous solution of proteins and other chemicals called plasma. Although in the past blood transfusions have used whole blood, the current trend is to collect and transfuse only those blood components required by a particular patient. This approach preserves the available blood supply and in many cases is better for the patient, since the patient is not exposed to unnecessary blood components.

Blood components are typically obtained from a donor following whole blood collection. A disposable blood collection set, including a harness (e.g., tubing and connectors), a phlebotomy needle and one or more collection bags, is utilized to collect the whole blood from the donor. In particular, the phlebotomy needle is inserted into the donor's arm and blood flows under gravity into a collection bag which may contain an anticoagulant. Thereafter, the whole blood may be provided to a blood-processing machine for separation into one or more desired components. The machine includes a rotatable separation chamber which subjects the whole blood to many times the force of gravity, thereby separating the various blood components according to their densities. That is, the more dense components, such as red blood cells (RBCs), accumulate within the chamber at its outer periphery, while the less dense components are withdrawn through an outlet port. When the separation process is complete, the RBCs remaining in the separation chamber are removed. Blood components may also be obtained through apheresis in which whole blood from the donor is directly provided to the blood processing machine for separation and collection. With this method, any uncollected blood components may be returned directly to the donor.

The collected blood components may then be stored before transfusion back to the donor or to some other patient. For example, the individual blood components, such as RBCs, may be refrigerated at approximately 4° C. for several days. Procedures are also known for freezing RBCs to further extend their shelf-life. For example, RBCs may be stored at approximately −80° C. or −160° C., depending on how they are prepared, for several years.

In particular, RBCs are typically preserved with glycerol, prior to freezing, which crosses the cell membranes. Without glycerol, the RBCs would not survive the freezing process. U.S. Pat. Reissue No. 33,924 to Valeri and entitled Apparatus and Method for Storing and Processing Blood discloses a method and apparatus for glycerolizing RBCs prior to freezing and also for washing the glycerol from thawed RBCs prior to transfusion. In particular, a three step process is used to introduce glycerol into a bag containing RBCs. First, the RBC bag is placed on a shaker platform operating at approximately 180 oscillations per minute, and 50ml of a glycerol solution is gravity fed into the bag. The shaker platform is then turned off for about five minutes, allowing the RBCs and glycerol solution to equilibrate. Next, the shaker platform is turned back on and a second volume of approximately 50 ml of glycerol solution is added to the bag. Again, the shaker platform is turned off and the RBCs and glycerol solution are allowed to equilibrate for approximately two minutes. The bag is then removed from the shaker platform and a third volume of approximately 400 ml of glycerol solution is added while an operator applies manual agitation to the bag.

The bag is then loaded onto a bag centrifuge device to concentrate the glycerolized RBCs. This results in the bag containing concentrated glycerolized RBCs and a supernatant glycerol solution. To remove the supernatant, the bag is placed in a plasma extractor. The bag may then be sealed in an overwrap bag and placed in a freezer operating at −80° C. As noted in the '924 patent, the entire process must be completed within four hours and results in glycerolized RBCs having a hematocrit of approximately 60%.

Thus, the prior art glycerolization process is a time-consuming and labor intensive task. It also requires a highly skilled operator to ensure that the glycerol solution is administered in the proper doses at the appropriate times. Improper administration of glycerol, which is an osmolite, may damage the RBCs. In particular, the RBCs may suffer osmolarity shock causing cellular damage if the glycerol is introduced too quickly.

The prior art method for washing the thawed, cryopreserved RBCs prior to transfusion is similarly time-consuming and labor intensive. More specifically, as described in the '924 patent, the bag of frozen, cryopreserved RBCs is placed in a heated bath for 20–25 minutes to thaw the RBCS. A machine, such as the Model 115 from Haemonetics Corp., which includes a shaker platform, a centrifuge drive unit and a wash bowl is then employed. First, 50 ml of a 12% sodium chloride solution is gravity fed into the bag and mixed with the thawed RBCs by agitation of the shaker. The shaker is then turned off for two minutes to equilibrate the two solutions. Then shaker is then turned back on and 100 ml of a 0.9% sodium chloride and 0.2% glucose solution is gravity fed into the bag and mixed therein. Again, the shaker is stopped for about two minutes to permit the solutions to equilibrate. The shaker is turned on once again and 150 ml of the sodium chloride/glucose solution is added. The shaker is then turned off for two minutes. As with the glycerol solution, the introduction of each volume of wash solution to the thawed RBCs is also a delicate process. In particular, the wash solution is also an osmolite and thus may cause the RBC membranes to burst if it is added too quickly.

The contents of the bag are then centrifuged to remove the wash solution and removed glycerol and the resulting RBCs are transferred to a collection bag. Just prior to transfusion, the washed RBCs are concentrated through centrifugation and removal of the supernatant. The final RBCs typically have a hematocrit below 40%.

As the '924 patent illustrates, the sensitivity of RBCs to osmolarity shock mandates repetitive, detailed steps that must be manually performed in order to avoid sudden changes in osmolite concentrations—both when preparing the RBCs for freezing and also when recovering stored RBCs prior to use. This results in a costly process limiting the use of cryopreservation and thereby placing greater demands on timely blood collection efforts. In addition, due to chemical and other concerns, commercially available glycerol solutions typically come in rubber-sealed, glass bottles, rather than plastic bags having tube connections. To access the glycerol, a needle or spike connection must be used, thereby creating an "open" system which means potentially contaminated air and other impurities may enter the system. Furthermore, due to its high viscosity, glycerol cannot be gravity fed through an anti-bacterial filter. Thus, any contaminants entering the system are likely to reach the RBCs. Although this does not limit the length of time that the RBCs may remain frozen, it does require that the subsequently thawed red blood cells be utilized within 24 hours or discarded.

SUMMARY OF THE INVENTION

It is an object of the present invention to provide an improved method for preparing red blood cells for freezing.

It is a further object of the present invention to provide an improved method for rapidly delivering a cryopreservation solution to red blood cells without causing osmolarity shock.

It is a further object of the present invention to provide an improved method for rapidly washing thawed red blood cells without causing osmolarity shock.

Briefly, the invention relates to a system for delivering a cryopreservation solution to red blood cells to permit long-term, frozen storage and for subsequently removing the cryopreservative during red blood cell recovery. The system preferably includes a controller that is operably connected to a shaker platform, a centrifuge drive unit and one or more variable-speed pumps. A display screen, printer and input device may also be connected to the controller. A cryopreservation harness is used to connect a cryopreservation solution to a unit of concentrated red blood cells, which may be placed on the shaker platform. The controller is configured to monitor and govern the delivery of cryopreservation to the red blood cells via the pump. In particular, the controller periodically determines the amount of cryopreservation solution already added to the red blood cells and, based on this value, calculates a new cryopreservation solution flow rate in accordance with a novel algorithm. The algorithm provides a linear increase in red blood cell osmolarity that is selected to reduce the risk of shock and to minimize the processing time. By dynamically adjusting the pump speed, the controller delivers cryopreservation solution at the calculated flow rates throughout the cryopreservation process.

During the recovery process, a recovery harness, which includes a separation bowl and a wash solution, is similarly loaded onto the system. The thawed red blood cells are preferably placed on the shaker platform and coupled to both the wash solution and the separation bowl by two pumps. For red blood cell recovery, the controller is configured to monitor and govern the delivery of a first volume of wash solution to dilute the red blood cells. In particular, the controller dynamically adjusts the rate at which a dilution volume of wash solution is delivered to the red blood cells pursuant to a second novel algorithm. The second algorithm, which is similarly dependent on a calculated volume of wash solution already delivered, provides a linear decrease in red blood cell osmolarity that is selected to minimize shock while reducing the dilution time. By dynamically adjusting the speeds of the two pumps, the controller delivers wash solution at the calculated flow rates throughout the dilution process. After the red blood cells have been diluted, they may be transferred to the separation bowl and additional wash solution may be introduced in order to wash any remaining cryopreservative from the cells.

In the preferred embodiment, the cryopreservation solution is preferably pumped through an anti-bacterial filter before reaching the red blood cells. By filtering the cryopreservation solution and thereby removing potential contaminants, a significantly longer shelf-life of the subsequently recovered red blood cells is enabled. In addition, during the recovery process, the thawed red blood cells are initially diluted with a volume of a hypertonic solution prior the introduction of the wash solution. The hypertonic solution has an osmolarity close to that of the thawed red blood cells and further reduces the risk of shock. Furthermore, additional wash cycles are preferably performed to remove the debris resulting from the disintegration of weak cells unable to survive the recovery process and the washed red blood cells are suspended in a preservation solution to extend their shelf-life even further. Each step of the cryopreservation and recovery processes, moreover, is automatically performed by the system under the management of the controller, significantly reducing error and the overall processing time.

BRIEF DESCRIPTION OF THE DRAWINGS

The above and further advantages of the invention may be better understood by referring to the following description in conjunction with the accompanying drawings, in which.

DETAILED DESCRIPTION OF THE PREFERRED EMBODIMENT

Figure 1:
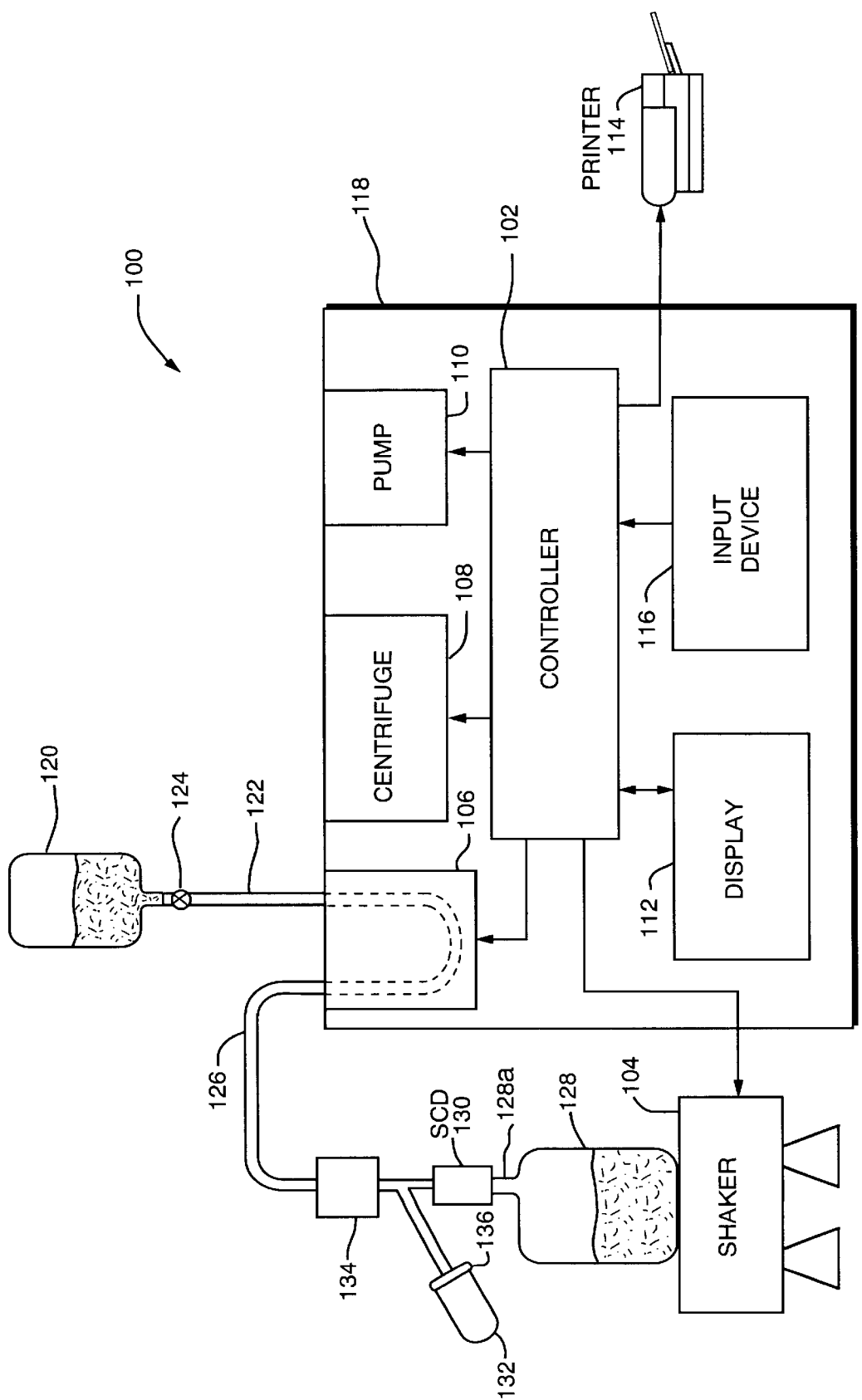
FIG. 1 is a highly schematic block diagram of the improved system of the present invention configured to prepare a unit of red blood cells for cryopreservation.

FIG. 1 is a block diagram of an improved cryopreservation/recovery system 100 in accordance with the present invention. The system 100 includes a controller 102, a shaker platform 104, a first pump 106, a centrifuge drive unit 108 and a second pump 110. The centrifuge drive unit 108 is preferably configured to receive a separation bowl as described below in connection with the washing of red blood cells. The controller 102 is operably connected to the shaker platform 104, the two pumps 106, 110 and the centrifuge drive unit 108 and may also be coupled to a plurality of input/output devices. For example, controller 102 is preferably coupled to a display screen 112 for presenting information to a system operator and to a printer 114 for printing reports and other information. A system operator may supply information to the controller 102 by means of an input device 116 (e.g., a keyboard and/or mouse). The two pumps 106 and 110, the centrifuge drive unit 108, the display 112, the input device 116 and the controller 102 may all be disposed in a housing 118.

In the preferred embodiment, the controller 102 includes one or more central processing units (CPU) and associated memory devices that may contain executable software instructions for implementing the steps of the invention as described below. The two pumps 106, 110 are preferably dual-direction, peristaltic pumps, providing approximately 1 ml of fluid per revolution. Each pump 106, 110 preferably includes an optical air detector (not shown) to determine whether air exists in the lines coupled to the pumps. Suitable components for the present invention are similar to the components in the Mobile Collection System (MCS) No. 8150 from Haemonetics Corp.

Cryopreservation of Red Blood Cells

First, approximately 450 ml of whole blood is collected from a donor in a primary bag containing an anticoagulant. It should be understood that the actual volume of whole blood that is collected and its corresponding hematocrit level may depend on the size of the separation bowl used during the recovery phase following cryopreservation. The whole blood may be stored in a conventional manner at approximately 4° C. Next, the whole blood is centrifuged to separate the red blood cells from the other blood components in a conventional manner. For example. the whole blood may be centrifuged at 1615 times the force of gravity for four minutes to separate the red blood cells. The equipment and procedures for centrifuging whole blood are well-known to those skilled in the art and need not be described herein. The separated red blood cells (RBCs) may also be stored at approximately 4° C. for a short time. Before the cryopreservation process begins, however, the RBCs and the cryopreservation solution are preferably warmed to room temperature (e.g., 22–30° C.).

Referring to FIG. 1, a cryopreservation harness is preferably loaded onto the system 100. More specifically, a bottle of cryopreservation solution 120 is connected to the first pump 106 by means of a first line 122. A conventional spike connector and drip chamber (not shown) may be used to connect line 122 to bottle 120 and a clamp or pneumatic valve 124 that is moveable from an open to a closed position may be located in line 122 to control the flow of cryopreservation solution to the first pump 106. In the preferred embodiment, the cryopreservation solution is a glycerol solution having a concentration of 57.1% by weight, which is generally available in 500 ml glass bottles. The cryopreservation solution 120 may be suspended from an intravenous (IV) pole (not shown) attached to housing 118. A second line 126 connects the first pump 106 to a container 128 of red blood cells. The container 128 preferably includes a tube section 128a which may be connected to second line 126 by means of a sterile connection device (SCD) 130. The SCD 130, such as the Model 312 from Terumo, is a well-known device for sterilely welding two tube segments together.

Disposed in the second line 126 are a pressure probe 132 and an associated anti-bacterial filter 134. The filter 134 is preferably a 0.2 μm hydrophilic filter, such as the Super IV-3 Air Eliminating Filter from Pall/Gelman Sciences, Inc. The pressure probe 132, which is preferably located between the filter 134 and the SCD weld 130, supplies a corresponding pressure signal to the main controller 108 to ensure that the SCD weld is not inadvertently resealed and that container 128 is not overfilled. To ensure the sterility of cryopreservation solution flowing through line 126, a 0.2 μm hydrophilic filter 136 is also utilized at pressure probe 132. In the preferred embodiment, lines 122 and 126 are a single, continuous line loaded through first peristaltic pump 106.

Figure 2A:
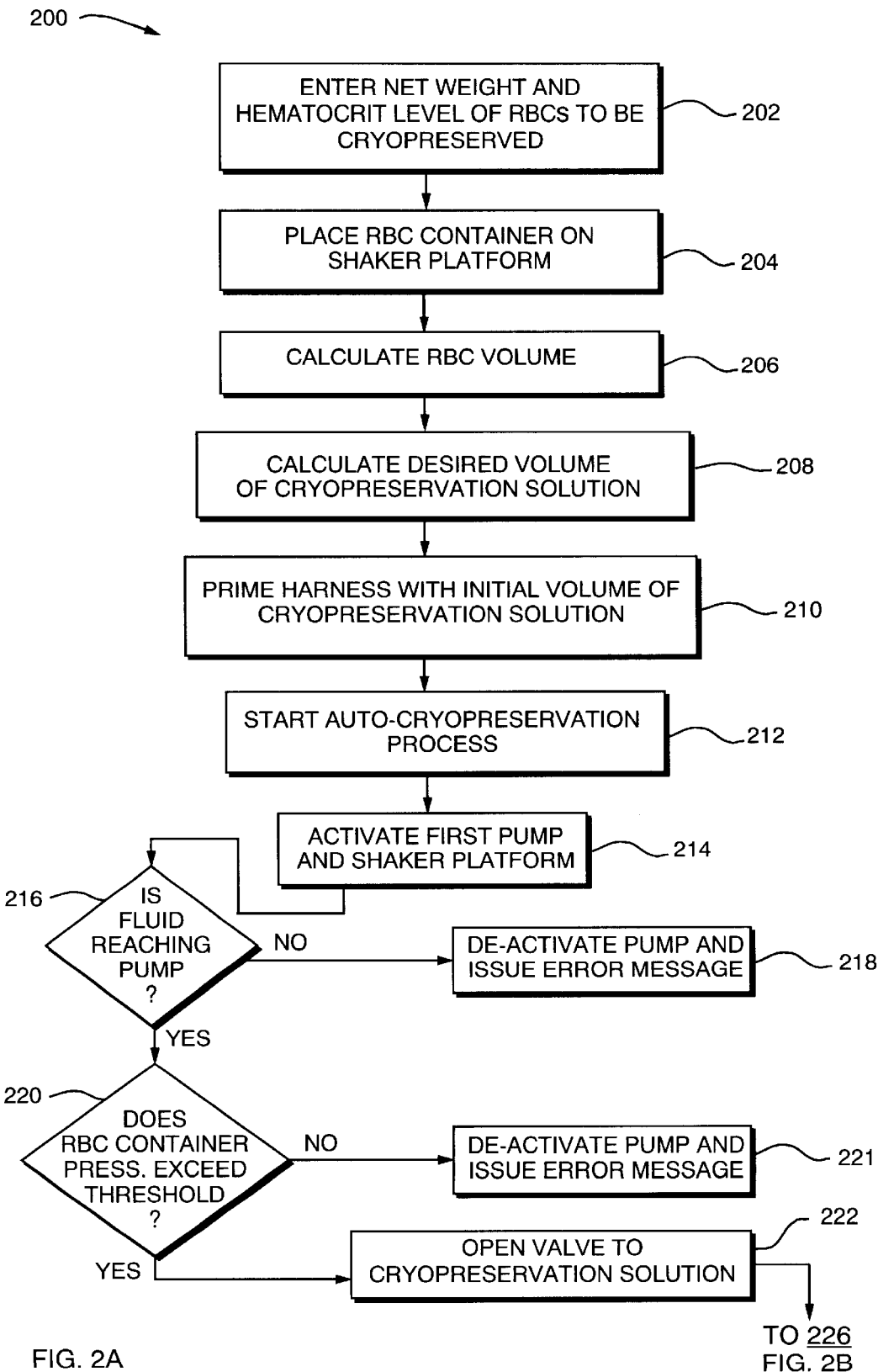
FIGS. 2A–B are flow diagrams of a preferred method for cryopreserving a unit of red blood cells.
Figure 2B:
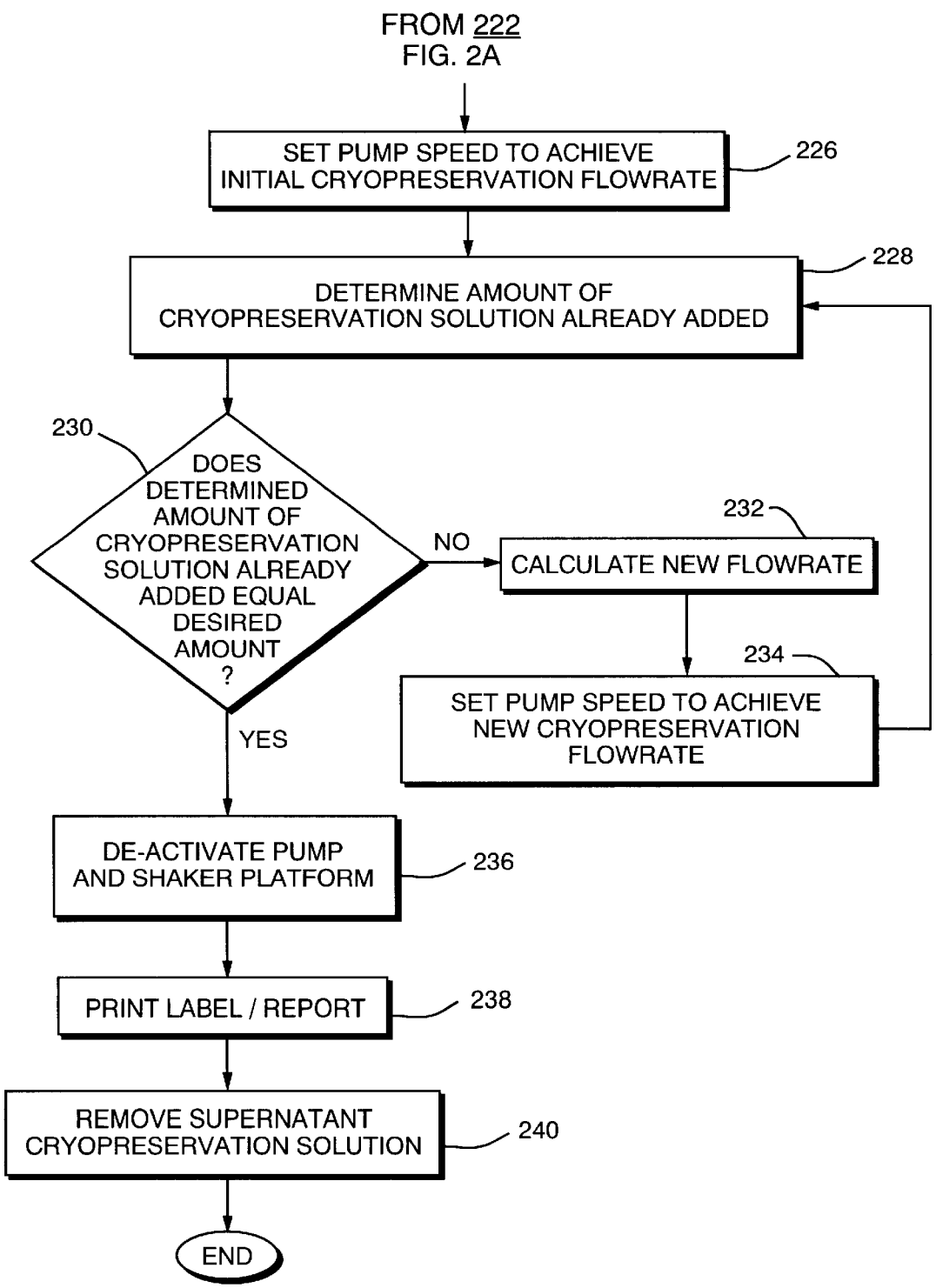

FIGS. 2A–B are flow diagrams of the steps 200 associated with the cryopreservation process in accordance with the present invention. After loading the cryopreservation harness onto the system 100 as described above, the system operator preferably enters the net weight and hematocrit level of the RBCs in container 128 into the system 100, as indicated at block 202, and places the container 128 onto the shaker platform 104, as indicated at block 204. The controller 102 then proceeds to calculate the volume of RBC concentrate within container 128 and also the desired volume of cryopreservation solution to be delivered to the RBC concentrate, as indicated by blocks 206 and 208. The volume of RBC concentrate, $V_i$, is preferably determined according to the following equation.

$$V_i = NW_i / [1.1 * Hct_i/100 + 1.026 * (1 - Hct_i/100)] \tag{1}$$

where, $NW_i$ is the net weight of concentrated red blood cells prior to cryopreservation (grams) and $Hct_i$ is the hematocrit level of the red blood cells before cryopreservation (%). The total volume of cryopreservation solution, $V_g$, to be mixed with the concentrated red blood cells is preferably computed in accordance with the following equation.

$$V_g = C_f/(C_i - C_f) * V_i * (1 - Hct_i/100 + Hct_i * W/1000) \tag{2}$$

where, $C_f$ is the target concentration of cryopreservative within the concentrated red blood cells following the cryopreservation process (%), $C_i$ is the concentration of cryopreservative in the cryopreservation solution (%), and W is the volumetric percentage of water in the concentrated red blood cells (%) The values for W, $C_i$ and $C_f$ may be entered into the system 100 by the operator through input device 116, or the controller 102 may be pre-configured in a conventional manner with corresponding default values. In the preferred embodiment, the main controller 102 is pre-configured with W set to 72%, $C_i$ set to 57.1% (the percentage of glycerol in its most commonly available form) and $C_f$ set to 40% which is the desired concentration of glycerol in the concentrated red blood cells for storage at −80° C.

Next, the operator pinches the drip chamber at bottle 120 to prime line 122 with an initial volume of cryopreservation solution, as shown at block 210. The valve 124, however, preferably remains closed at this point. The operator then engages the controller 102 through input device 116, as shown at block 212 (e.g., by pressing a "start" button). The controller 102 activates the first pump 106 and the shaker platform 104, which preferably operates at 3 Hz and 1.5 inches peak-to-peak amplitude, as indicated at block 214. The first pump 106 is preferably activated at an initial flow rate of 30 ml/minute and, as indicated at block 216, the controller 102 checks for fluid reaching pump 106 by monitoring the output of the corresponding the air detector. If no fluid is detected after 10 ml of pumping action, the controller 102 de-activates the pump 106 and issues an error message on display 112, as shown at block 218, indicating that the operator should check for occlusion in line 122. If fluid is detected, the controller 102 next monitors the increase in pressure in container 128 via pressure probe 132, as indicated at block 220.

When the pressure exceeds 100 mm Hg, the controller 102 preferably opens valve 124, as shown by block 222, and begins counting the volume of cryopreservative solution delivered to container 128 by pump 106 based on the number of pump revolutions. If the pressure does not reach 100 mm Hg after approximately 5 ml of pumping action following the detection of fluid, the controller 102 preferably deactivates the pump 106 and issues an error message on display 112, as indicated by block 224. The error message may request the operator to check lines 122, 126 for leaks. Assuming the pressure reached the desired level and valve 124 was opened, the controller 102 proceeds to deliver the predetermined volume of cryopreservation solution, $V_g$, to the red blood cells in container 128.

Due to the large osmolarity differential between the 57.1% glycerol solution (e.g., approximately 7230 mOsm/KgH$_2$O) and the concentrated red blood cells in container 128 (e.g., approximately 320 mOsm/KgH$_2$O), the red blood cells are highly susceptible to hypertonic shock and cell damage during cryopreservation. That is, even though glycerol actually diffuses across the cell membranes and is thus, in the strict sense, not a "true" osmolite, the high osmolarity differential between the RBCs and the glycerol solution causes water to be "pumped" out of the RBCs at a much higher rate than glycerol diffuses into the cells. The cell membranes are thus subject to high stresses, especially during the initial phases of the process, risking possible cell destruction. As more and more glycerol diffuses into the red blood cells, their osmolarity increases, thereby reducing the osmolarity differential with the cryopreservative solution and the consequent risk of shock. Under the prior art technique, glycerol is initially added in small, fixed doses to limit possible RBC damage. This approach, however, is time-consuming, labor intensive and error prone.

With the present invention, the cryopreservation solution is preferably delivered to the RBCs continuously. In particular, cryopreservation solution is delivered in such a way that the osmolarity of the red blood cells evolves linearly over time (e.g., dOsmolarity/dt=constant). Thus, the present invention takes advantage of the increasing osmolarity of the red blood cells to increase the rate at which cryopreservative solution is delivered. Furthermore, by increasing the rate at which cryopreservative solution is added to the RBCs, the overall time needed to complete the process may be significantly reduced.

In particular, the main controller 102 continuously calculates the desired flow rate of cryopreservation solution and dynamically adjusts the operating speed of pump 106 to achieve the desired flow rate. The cryopreservation flow rate, $F_g$, is preferably calculated according to the following equation.

$$F_g = K[V_i*(W*\text{Hct}_i/100) + V_g]^2 / [V_i*(W*\text{Hct}_i/100)*(O_i - O_g)] \quad (3)$$

where,

K is the selected rate of increase in osmolarity of the red blood cells (mOsm/Kg H$_2$O/min.), $V_i$ is the volume of red blood cells before cryopreservation (ml), $V_g$ is the volume of cryopreservative solution that has already been added to the red blood cells prior to the current flow rate calculation (ml), $O_i$ is the osmolarity of the red blood cells before cryopreservation (mOsm/Kg H$_2$O), and $O_g$ is the osmolarity of the cryopreservation solution (mOsm/Kg H$_2$O).

Since the determination of the cryopreservative solution flow rate is dependent on the volume of cryopreservation solution already added to the red blood cells ($V_g$), an initial flow rate must be determined by controller 102 independent of equation (1). The initial flow rate, $F_o$, is preferably determined as follows.

$$F_o = K*V_i*(W*\text{Hct}_i/100)/(O_i - O_g) \quad (4)$$

Additionally, the volume of cryopreservation solution processed by the red blood cells at any given time, t, is calculated as follows.

$$V_g = K*V_i*(1 - 0.28*\text{Hct}_i/100)*t/(O_i - O_g - K*t) \quad (5)$$

And, the total time, T, needed to deliver the requisite volume of cryopreservation solution to the red blood cells is calculated as follows.

$$T = V_g*(O_i - O_g)/K/[V_i*(1 - 0.28*\text{Hct}_i/100) + V_g] \quad (6)$$

Main controller 102 is preferably pre-configured in a conventional manner to determine each of these values according to the above-identified equations (3)–(6). It should be understood that parameters K, $O_i$ and $O_g$ may be entered by the operator or pre-configured within a memory device of controller 102. In the preferred embodiment, the controller 102 is pre-configured with K set to approximately 500, $O_i$ set to 320 and $O_g$ set to 7230.

As shown in block 226, the controller 102 begins delivering cryopreservation solution from bottle 120 at the initial flow rate, $F_o$, by setting the operating speed of pump 106 accordingly. Thereafter, the controller 102 continuously determines the amount of cryopreservation solution, $V_g$, that has been added to container 128 using equation (5), as shown at block 228. Next, the controller 102 determines whether the computed volume of cryopreservation solution equals the desired volume selected to obtain the chosen concentration, as indicated at block 230. If not, controller 102 calculates a new flow rate, $F_g$, from equation (3), as shown at block 232. The pump 106 is then adjusted to achieve this new flow rate, as shown at block 234. Controller 102 may wait until at least 1 ml of cryopreservation solution has been pumped at the initial flow rate, $F_o$, before making its first calculation and corresponding adjustment.

In the preferred embodiment, the controller 102 calculates new flow rate values, $F_g$, and adjusts the pump speed on a real-time basis in accordance with a software loop executing the above-described process. Depending on the operating characteristics of the processor and memory components of the controller 102, calculations and adjustments to the pump speed may be made on the order of every 200 ms. Nonetheless, it should be understood that controller 102 may be programmed to calculate a new flow rate $F_g$ at any predetermined time intervals. It should also be understood that if the change in flow rate is substantially less than smallest increment by which the pump may be adjusted (e.g., under ½ ml/min. for a pump adjustable in 1 ml/min. increments), no change in pump speed is made.

Once the total volume of cryopreservation solution, $V_g$, as determined above, has been delivered to container 128, controller 102 deactivates pump 106 and, shortly thereafter (e.g., 30 seconds later), stops the shaker 104, as indicated at block 236. The tube segment 128a from container 128 may then be cut from line 126 and heat sealed. A label identifying the unit of concentrated RBCs, the operator, donation center, date, initial blood unit net weight, initial blood unit hematocrit, initial blood unit volume, volume of cryopreservation solution added and the elapsed time of the cryopreservation process, among other information, may be printed by the controller 102 on printer 114, as indicated by block 238. The label may be affixed to the container 128 for identification purposes.

The total volume of fluid in container 128 following the cryopreservation process is about 700–800 ml including about 200 ml of "absolute" RBCs (and a small volume of plasma) suspended in approximately 400–500 ml of cryopreservation solution. Preferably, container 128 is subject to bag centrifugation by the system operator and the supernatant cryopreservation solution is removed in a conventional manner, leaving approximately 200 ml of absolute RBCs (approximately 300 ml total volume) to be frozen, as shown at block 240. Bag centrifugation, which involves spinning the container at high rotational speeds, is well-known to those skilled in the art and need not be described in detail herein. This completes the cryopreservation process and the glycerolized-RBCs may be frozen at –80° C.

It should be understood that depending on the type of anti-bacterial filter 134 utilized with system 100, the pressure in line 126 may need to be kept within certain limits. For example, with a Pall/Gelman Sciences, Inc. antibacterial filter, the pressure should not exceed 45 psi. To keep the pressure at filter 134 within this limit, the maximum flow rate permitted by controller 102 should not exceed 80 ml/min. Thus, if the calculated flow rate of cryopreservation solution per equation (3) calls for a corresponding pump speed in excess of 80 ml/min., the controller 102 will nonetheless not exceed 80 ml/min.

As shown, the present invention provides a substantially improved system for preparing red blood cells for cryopreservation. It should be understood that other cryopreservation solutions, besides glycerol, may be utilized with the present invention, such as hydroxyethyl starch (HES), dimethyl sulfoxide (DMSO), etc. It should be further understood that other blood components, besides red blood cells, may be subject to the cryopreservation procedure described above. It should also be understood that other target concentrations of cryopreservative, $C_p$, may be selected for storage at other temperatures (e.g., 30% for storage at −160° C.).

Recovery of Frozen Red Blood Cells

Figure 3:
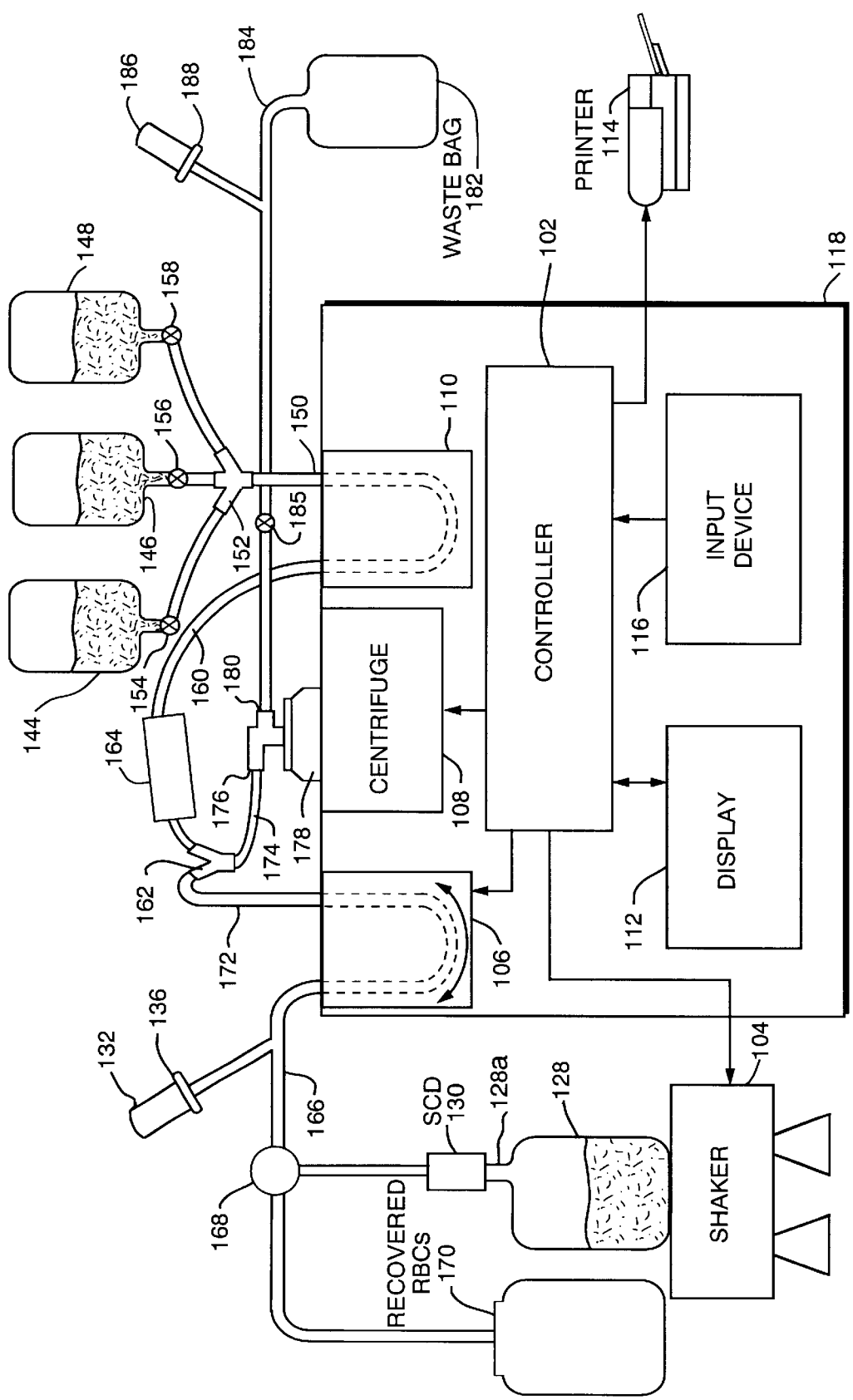
FIG. 3 is a highly schematic block diagram of the improved system of FIG. 1 configured to recover a unit of cryopreserved red blood cell.
Figure 4A:
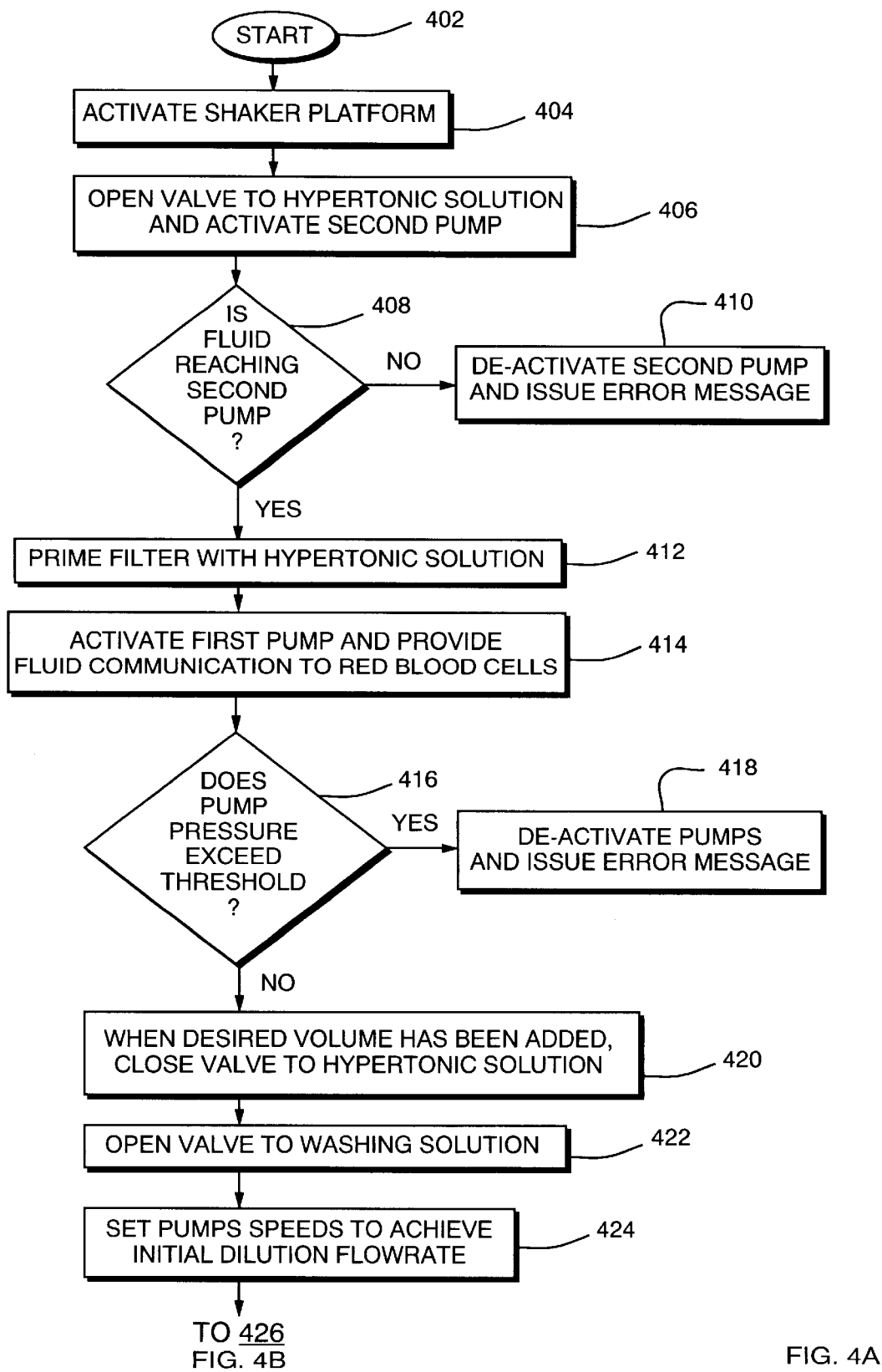
FIGS. 4A–D are flow diagrams of the preferred method for recovering previously frozen red blood cells.
Figure 4B:
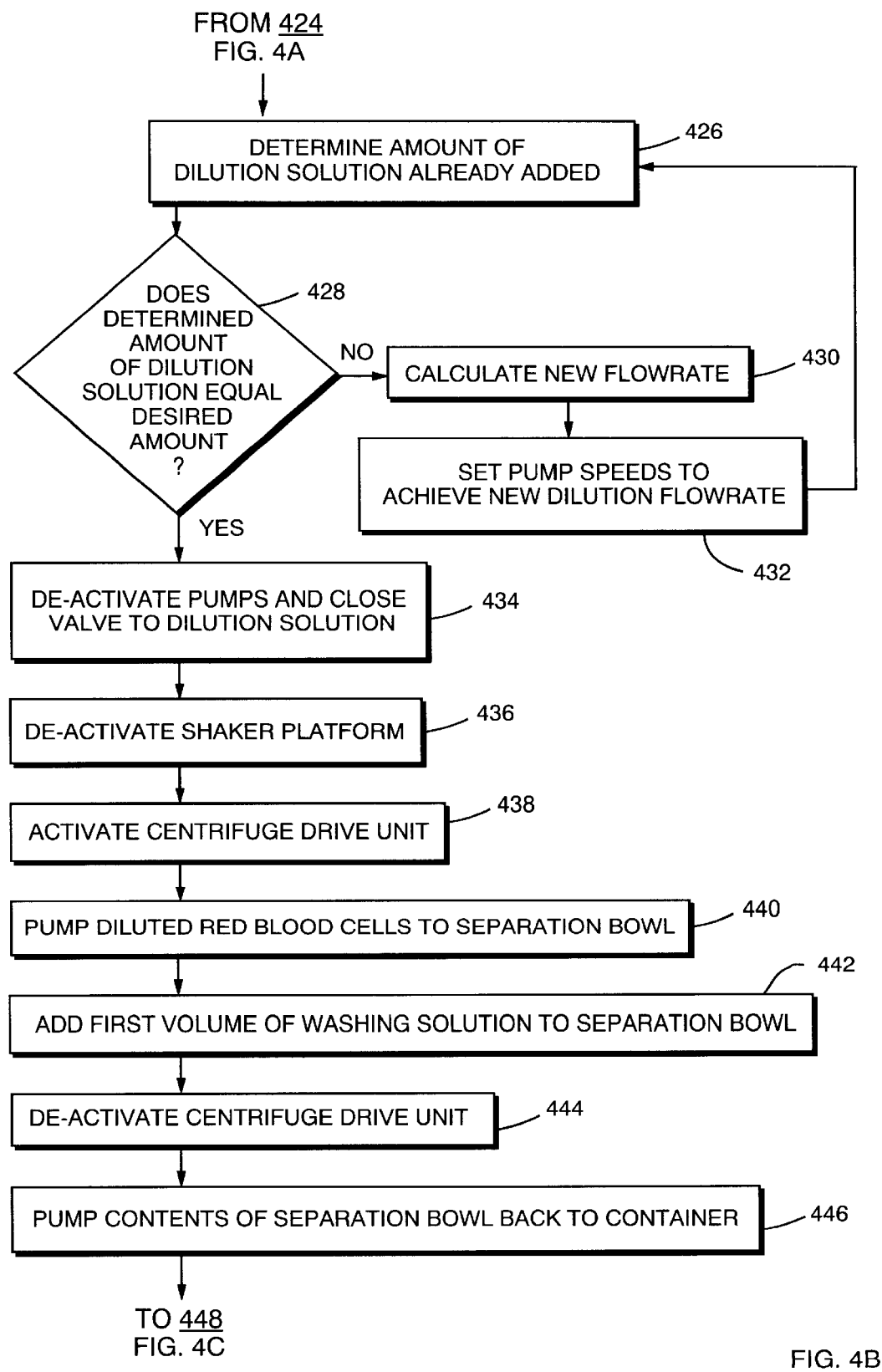
Figure 4C:
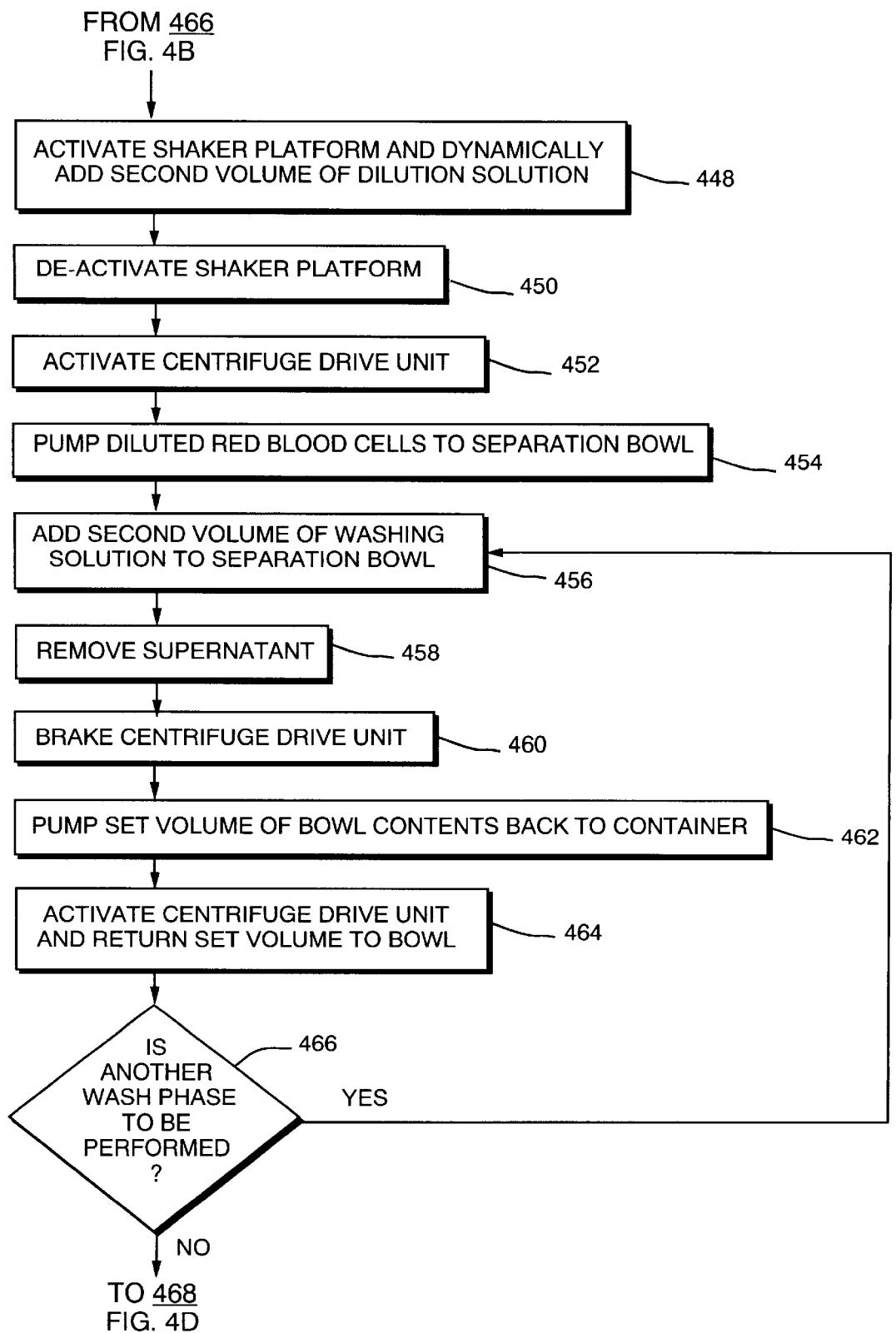
Figure 4D:
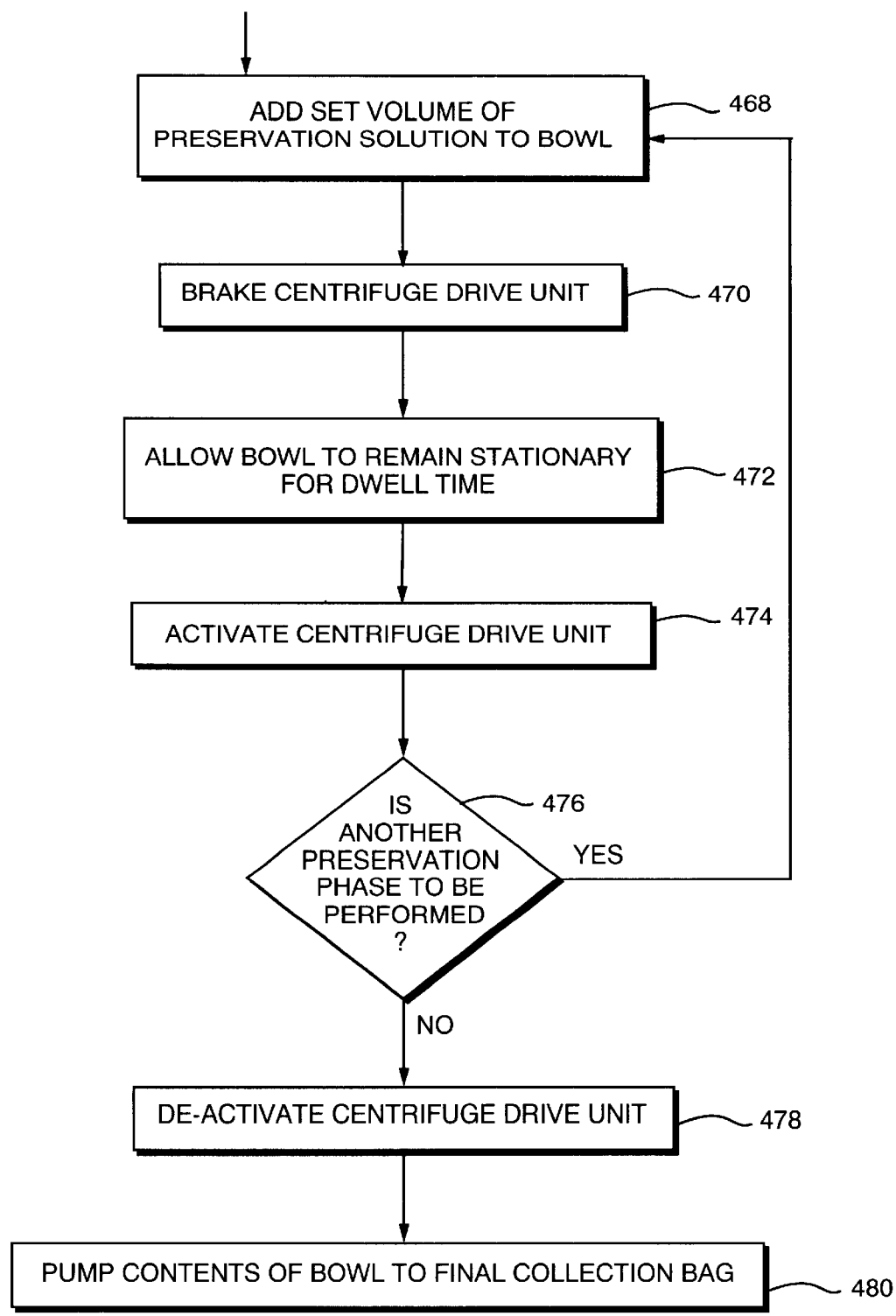

FIG. 3 is a block diagram of the system 100 configured to recover previously frozen red blood cells. As described above, system 100 includes a controller 102 operably coupled to two pumps 106, 110, a centrifuge drive unit 108, a shaker platform 104, a display 112 and a printer 114. An input device 116 allows a system operator to enter data and other information into the system 100. To recover previously frozen red blood cells in container 128, a separate recovery harness is preferably loaded onto system 100. In particular, three different solution bags 144, 146 and 148 are connected to pump 110 by means of a first line 150 and a three-way connector 152. Bag 144 preferably contains a preservative solution, such as AS-3 from Haemonetics Corp. Bag 146 preferably contains a washing solution (e.g., a 0.9% sodium chloride and 0.2% glucose solution) and bag 148 preferably contains a hypertonic solution (e.g., a 12% Sodium Chloride solution). The hypertonic solution contained in bag 148 preferably has an osmolarity almost equal to the osmolarity of the thawed RBCs in container 128. Associated with each bag 144, 146 and 148 is a corresponding pneumatic valve 154, 156, 158 which may be moved from an open to a closed position.

A second line 160 connects pump 110 to a Y-connector 162 and preferably includes an anti-bacterial filter 164, which may be a 0.22μm hydrophilic filter. A third line 166 which includes a two-way valve 168 is connected to one side of pump 106. Connected to one side of valve 168 by means of the SCD 130 is the tube segment 128a of container 128, which is again placed on the shaker platform 104. The red blood cells in container 128 are preferably thawed in a warm bath prior to being placed on shaker platform 104 as is well known. A final, recovered RBC collection bag 170 may be pre-connected to the other side of the two-way valve 168. Disposed within third line 166 are the pressure probe 132 and associated filter 136. A fourth line 172 connects pump 106 to the Y-connector 162. The outlet of the Y-connector 162 is coupled by a fifth line 174 to an inlet 176 of a separation bowl 178 which may be loaded in the centrifuge drive unit 108. An outlet 180 of centrifugation bowl 178 may be connected to a waste bag 182 by means of a sixth line 184 having a pneumatic valve 185. A second pressure probe 186 and associated anti-bacterial filter 188 are preferably disposed in the sixth line 184. In the preferred embodiment, lines 150 and 160 and lines 172 and 166 are single, continuous lines loaded through corresponding pumps 110, 106.

Separation bowl 178 may be a 275 ml spun volume, blow-molded bowl with a diverter and shortened plasma core, which may be similar to the series of 275 ml blow molded bowls from Haemonetics Corporation. The diverter (not shown) divides the interior of the bowl into two chambers (a separation chamber and a wash chamber), which facilitates the washing of red blood cells.

Dilution of Thawed Red Blood Cells With Hypertonic Solution

Assuming the thawed red blood cells have a 40% cryopreservative (e.g., glycerol) concentration, then the osmolarity of the thawed red blood cells should be on the order of 5200 mOsm/KgH$_2$O. The osmolarity of a conventional washing solution (such as the 0.9% sodium chloride/0.2% glucose solution) is approximately 300 mOsm/KgH$_2$O. This high osmolarity differential exposes the red blood cells to hypotonic shock (i.e., they rapidly take on water) and consequent cellular damage during the recovery process. To reduce the risk of hypotonic shock, the red blood cells are preferably initially diluted with a hypertonic solution having an osmolarity on the same order as the thawed red blood cells. By diluting the thawed red blood cells with the hypertonic solution, some cryopreservative solution is drawn out of the cells and the RBC supernatant volume is increased, lowering the risk of RBC hypotonic shock during the recovery process.

The addition of the hypertonic solution also provides a slight reduction in red blood cell osmolarity. More specifically, the osmolarity of the thawed red blood cells following dilution with a hypertonic solution, $O_{ph}$, is given by the following equation.

$$O_{ph}=(V_t{*}O_t+V_h{*}O_h)/(V_t+V_h) \quad (7)$$

where, $V_t$ is the volume of the thawed red blood cells (ml), $O_t$ is the osmolarity of the thawed red blood cells (mOsm/KgH$_2$O), $V_h$ is the volume of hypertonic solution added to the thawed red blood cells (ml), and $O_h$ is the osmolarity of the hypertonic solution (mOsm/KgH$_2$O). In the preferred embodiment, 50 ml of a 12% Sodium Chloride hypertonic solution having an osmolarity of about 4000 mOsm/KgH$_2$O is utilized to achieve a desirable osmolarity for diluted red blood cells of 4800–5300 mOsm/KgH$_2$O as well as a desired supernatant buffer volume. Thus, one of the first steps of the recovery process is to mix approximately 50 ml of hypertonic solution with the thawed red blood cells.

FIGS. 4A–D are flow diagrams of the steps 400 corresponding to the preferred red blood cell recovery process. Once the recovery harness is properly loaded and the container 128 is placed on the shaker platform 104, the system operator preferably starts the system 100, as indicated at block 402. In response, the controller 102 activates the shaker platform 104, which preferably operates at 3 Hz and 1.5 inches peak-to-peak amplitude, as indicated at block 404. Additionally, valve 158, which is connected to the bag of hypertonic solution 148 (preferably loaded with 50 ml of a 12% sodium chloride solution), is opened and pump 10 is activated to move fluid from right to left (relative to FIG. 3) toward filter 164 at a pump speed of approximately 60 ml/min., as shown at block 406. The controller 102 also monitors the air detector associated with pump 110. In particular, controller 102 checks whether air is still being sensed despite approximately 5 pump revolutions at pump 110, as indicated at block 408. If so, controller 102 preferably de-activates pump 110 and issues an error message on display 112, as indicated at block 410. Once fluid is sensed at pump 110, controller 102 primes filter 164 with approximately 5 ml of hypertonic fluid by counting the fluid passing pump 110, as indicated at block 412.

The controller 102 next activates pump 106 in a right to left direction (relative to FIG. 3) and moves valve 168 to provide fluid communication to container 128, as indicated at block 414. Hypertonic solution from bag 148 flows to pump 110, through filter 164 and Y-connector 162 to pump 106. From pump 106, the hypertonic solution flows through valve 168 and into container 128. Preferably, controller 102 operates pump 110 at a flow rate of 150 l/min. and pump 106 at approximately 5% less than the operating speed of pump 110. By running pump 106 at a 5% delta from pump 110, controller 102 ensures that little or no air is introduced into container 128. The controller 102 also monitors the pressure at pump 110 to ensure that it remains within certain limits, as indicated at block 416. If the pressure at pump 110 exceeds the range ±150 mm Hg, for example, controller 102 preferably de-activates both pumps 106, 110 and issues an error message, as shown at block 418. When the desired amount of hypertonic solution has been moved past pump 110 (e.g., 50 ml taking into account the volume in the various lines), valve 158 at the hypertonic solution bag 148 is closed, as indicated at block 420, completing the initial dilution of the thawed red blood cells with the hypertonic solution.

Dilution of Thawed Red Blood Cells With Washing Solution

The thawed RBCs are also diluted with a desired volume of washing solution from solution bag 146. However, the osmolarity of the thawed RBCs following dilution with hypertonic solution is approximately 4900 mOsm/KgH$_2$O, whereas the osmolarity of washing solution, such as 0.9% sodium chloride/0.2% glucose solution, is approximately 300 mOsm/KgH$_2$O, risking hypotonic shock, as washing solution is added to the red blood cells (because water from the washing solution enters the cells faster than cryopreservative diffuses out of the cells, causing them to swell). To minimize the risk, and to also minimize the washing time, the controller 102 dynamically adjusts the rate at which the desired dilution volume of washing solution is delivered to the RBCs so as to linearly decrease the RBC osmolarity over time (e.g., dOsmolarity/dt=constant). By maintaining a constant decrease red blood cell osmolarity as additional washing solution is added, the red blood cells are spared hypotonic shock while still causing some of the cryopreservative to be diffused out of the cells.

The flow rate, $F_s$, may be determined as a function of the washing solution already processed by the red blood cells according to the following equation.

$$F_s = K_D [V_i^*(W^*\text{Hct}_i/100) + V_s]^2 / [V_i^*(W^*\text{Hct}_i/100)^*(O_i - O_s)] \quad (8)$$

where, $K_D$ is the desired osmolarity rate decrease (mOsm/KgH$_2$O/min.), $V_i$ is the volume of the thawed red blood cells after dilution with the hypertonic solution (ml), Hct$_i$ is the hematocrit level of the thawed red blood cells after dilution with the hypertonic solution (%), $V_s$ is the volume of washing solution that has already been delivered to the thawed red blood cells (ml), $O_i$ is the osmolarity of the thawed red blood cells after dilution with the hypertonic solution (mOsm/KgH$_2$O), and $O_s$ is the osmolarity of the washing solution (mOsm/KgH$_2$O).

Since the determination of the washing solution flow rate is dependent on the volume of washing solution already delivered to the red blood cells, $V_s$, an initial flow rate must be determined independent of equation (8). The initial washing solution flow rate, $F_{so}$, is preferably determined as follows.

$$F_{so} = K_D^* V_i^*(W^*\text{Hct}_i/100)/(O_i - O_s) \quad (9)$$

The volume of washing solution processed by the thawed red blood cells at any given time, t, is calculated as follows.

$$V_s = K_D^* V_i^*(W^*\text{Hct}_i/100)^*t/(O_i - O_s - K_D^*t) \quad (10)$$

Similarly, the total time, T, needed to deliver the desired dilution volume of washing solution is calculated as follows.

$$T = V_s^*(O_i - O_s) K_D / [V_i^*(W^*\text{Hct}_i/100) + V_s] \quad (11)$$

The osmolarity of the red blood cells, $O_{s1}$, after dilution with the desired volume, $V_{s1}$, of washing solution is provided by the following equation.

$$O_{s1} = (V_h^* O_{ph} + V_{s1}^* O_s)/(V_h + V_{s1}) \quad (12)$$

To obtain a final osmolarity of approximately 2835 mOsm/KgH$_2$O, the red blood cells should be diluted with approximately 340 ml of washing solution, which is simply a function of the volume of container 128. More specifically, assuming container 128 has a capacity of 800 ml and already contains 350 ml of cryopreserved RBCs and 50 ml of hypertonic solution, then only 340 ml or so of washing solution may still be added without exceeding the container's capacity. Accordingly, controller 102 proceeds to deliver a total volume of 340 ml of washing solution to the red blood cells in accordance with the flow rate as periodically determined by equation (8).

In particular, upon closing valve 158, controller 102 opens valve 156 to the washing solution, as shown at block 422. Then, after the last of the hypertonic solution has reached container 128 and the washing solution is about to enter container 128 (i.e., sufficient volume has been moved past pump 110 to fill the intermediary lines and components), controller 102 preferably starts delivering washing solution to container 128 at the initial flow rate, $F_{so}$, per equation (9), as indicated at block 424. Controller 102 also begins counting the total volume of washing solution being delivered to container 128 and may display this running value on display 112. The controller 102 continuously determines the amount of washing solution delivered to the thawed red blood cells, as indicated at block 426, and decides whether this amount equals the desired amount (e.g., 340 ml), as indicated at block 428. If not, controller 102 recalculates the washing solution flow rate per equation (8) based on the current volume already delivered to the red blood cells, as indicated at block 430, and adjusts the corresponding speeds of pumps 110 and 106 to achieve the new flow rate, as indicated at block 432. Again, controller 102 preferably calculates new flow rate values, $F_s$, and adjusts the pump speed on a real time basis (e.g., on the order of every 200 ms).

Controller 102 also monitors the pressure at pump 106 to ensure that it remains within a selected range (e.g., ±150 mm Hg). If the pressure exceeds the selected range, controller 102 preferably de-activates pumps 106 and 110 and issues a warning or error message on display 112.

When the desired amount of washing fluid has been delivered to the red blood cells in container 128, controller 102 preferably de-activates the pumps 106, 110 and shuts off the supply of washing solution from bag 146 by closing valve 156, as indicated at block 434. Controller 102 preferably allows the shaker platform 104 to continue operating for an additional 10 seconds after de-activating the pumps 106, 110, as indicated at block 436.

Supernatant Removal

The container 128 now includes the volume of thawed red blood cells plus the dilution volumes of hypertonic and washing solutions from bags 148, 146, respectively. System 100 preferably separates the lighter phases of this solution (i.e., the supernatant) from the red blood cells through centrifugation. In particular, controller 102 activates the centrifuge drive unit 108 to spin centrifuge bowl 178 at approximately 8000 rpm, as indicated at block 438. Controller 102 next activates pump 106 in a left to right direction (relative to FIG. 3) to pump red blood cells from container 128 to centrifuge 178, as shown at block 440. Pump 106 may be operated at the maximum bowl 178 filling rate (e.g., 200 ml/min.). Controller 102 also counts the volume of fluid entering the centrifuge bowl 178 based on pump revolutions. Rotation of the centrifuge bowl 178 drives the heavier red blood cells outwardly against the inner surface of the bowl, while the supernatant (including hypertonic and wash solutions) collect in an annular zone located radially inward from the red blood cells. This supernatant is forced through the outlet 180 of bowl 178 and is collected in waste bag 182. Bowl 178 preferably includes an optical line sensor (not shown) which monitors the fluid exiting the bowl 178 to ensure that the more light absorbent red blood cells are not being discharged into the waste bag 182.

First Rinse Phase

With the bowl 178 still spinning, a volume (e.g., 100 ml) of washing solution is preferably added through operation of pump 110 at a constant flow rate (e.g., 50 ml/min.), as indicated at block 442. A corresponding volume (e.g., 100 ml) of supernatant, which includes hypertonic and wash solutions, is also removed. Controller 102 then de-activates centrifuge drive unit 108, stopping the bowl 178 and allowing the RBCs and remaining supernatant to re-mix, as indicated at block 444, for approximately 45 seconds.

Second Dilution of Thawed Red Blood Cells With Washing Solution

Next, the contents of the separation bowl 178 (approximately 280 ml) are preferably pumped back to container 128 through operation of pump 106 in a right-to left direction (relative to FIG. 3), as indicated at block 446. The pump speed may be about 200 ml/min. When the contents of bowl 178 have been returned to container 128, the controller 102 preferably activates the shaker platform 104 and delivers a second volume of wash solution from wash bag 146 to container 128, as indicated at block 448. More specifically, the controller 102 preferably delivers approximately 410 ml of wash solution, pursuant to the initial and dynamic flow rate equations (9) and (8), respectively, as described above in connection with steps 424 and 432. Again, the 410 ml of wash solution is simply a function of the capacity of container 128. In particular, since container 128 has about 250–260 ml (i.e., the bowl volume) of fluid an additional 410 ml will keep the total volume below its capacity (e.g., 800 ml). After the second volume of wash solution has been added to the red blood cells, controller 102 deactivates the shaker platform 104, as indicated by block 450. The RBCs have now been diluted with one volume of hypertonic solution and two volumes of wash solution. The osmolarity of RBCs should be close to the osmolarity of wash solution. The next step is to wash the remaining cryopreservative out of the RBCs.

It should be understood that additional dilutions may be performed on the thawed red blood cells by repeating the above steps.

Washing Phase

In the preferred embodiment, the system 100 performs five (5) separate washing phases with the diluted red blood cells in the centrifuge bowl 178. The washing phases are utilized to complete removal of cryopreservative within the RBCs and to remove any debris (e.g., broken cell membranes, free hemoglobin, etc.) from weak cells unable to survive the freezing and recovery process intact. For each wash phase, the volume of washing solution, its flow rate into the bowl 178 and the equilibrium time, as discussed, below are selected so that the osmolarity of RBCs evolves linearly over time. First, the controller 102 activates the centrifuge drive unit 108 so as to rotate bowl 178 at approximately 8000 rpm, as indicated at block 452, and pumps the diluted red blood cells from container 128 to the centrifuge bowl 178 through pump 106, as indicated at block 454. The pump speed may be on the order of 150 ml/min. at the beginning and 50 ml/min. at the end of the transfer. Next, the controller 102 proceeds to deliver approximately 150 ml of washing solution from bag 146 to spinning bowl 178, as indicated at block 456. The washing solution may be delivered at approximately 50 ml/min. These values have been empirically determined to provide a generally linearly change in RBC osmolarity. The supernatant generated within bowl 178 is removed and collected in waste bag 182, as shown at block 458. After the desired volume of wash solution has been added and the supernatant removed, controller 102 activates the braking mechanism of the centrifuge drive unit 108 and the bowl 178 is stopped, as shown at block 460. It typically takes approximately 15 seconds to stop the bowl 178 from spinning. The bowl 178 preferably remains stationary for a predetermined equilibrium delay period (e.g., 45 seconds). The equilibrium delay allows the RBC osmolarity to continue to evolve.

During the equilibrium delay, a set volume (e.g., 20 ml) of the bowl's contents may be pumped to the container 128 by pump 106, as indicated at block 462. This allows the bowl head to be re-aspirated and limits red blood cell loss during the next wash phase. Controller 102 next activates the centrifuge drive unit 108 to spin the bowl 178 at approximately 8000 rpm for a preset amount of time (e.g., 60 seconds) and returns the previously removed volume (20 ml) of fluid to the bowl 178, as indicated by block 464. This completes the first wash phase.

Controller 102 next determines whether another wash phase is to be performed, as shown at block 466. If so, 102 controller preferably repeats steps 456 to 466. As indicated, in the preferred embodiment, five wash phases are performed on the diluted red blood cells. The second wash phase preferably utilizes approximately 300 ml of washing solution delivered at about 100 ml/min., while the third through fifth wash phases each utilize 300 ml of washing solution delivered at 150 ml/min.

Suspension of Recovered Red Blood Cells in Preservation Solution

After completion of the wash cycles, controller 102 proceeds to suspend the washed red blood cells in a preservation solution. The suspension of washed red blood cells may performed in multiple phases. More specifically, with bowl 178 spinning at approximately 8000 rpm, a preset volume (e.g. 80 ml) of a preservation solution from bag 144 is delivered to the bowl 178 preferably at a constant flow rate (e.g., 80 ml/min.), as shown at block 468. The centrifuge drive unit 108 is then braked, stopping the bowl 178, as indicated at block 470. To increase the final hematocrit of the RBCs, the valve 185 to the waste bag 182 is preferably closed during braking, except for the last preservation cycle when it is opened, thereby allowing additional supernatant to be removed and collected in the waste bag 182. The bowl 178 is also allowed to remain stationary for a predetermined dwell time (e.g., 45 seconds), as indicated at block 472. This dwell time allows the contents of the bowl (i.e., washed red blood cells and preservation solution) to inter-mix and achieve a homogenous red blood cell suspension. After the dwell time, the centrifuge drive unit 108 is re-started and bowl 178 is spun at approximately 8000 rpm long enough to achieve adequate red blood cell sedimentation (e.g., 60 seconds), as shown at block 474.

Controller 102 next determines whether the suspension of washed red blood cells is complete, as shown at block 476. If not, controller 102 preferably repeats steps 468 to 476 as described above. In the preferred embodiment, the controller 102 performs one preservation cycle. At this point, the red blood cells have been washed of cryopreservative and are suspended in a preservation solution. Controller 102 de-activates the centrifuge drive unit 108, as shown at block 478, and then pumps the washed and suspended RBCs into the final collection bag 170, as indicated at block 480. The RBCs are moved by operating pump 106 in a right-to-left direction (relative to FIG. 3) at a flow rate of approximately 20 ml/min.

By replacing the supernatant wash solution with a preservation solution, filtering the cryopreservation solution during cryopreservation and washing the RBCs (to remove weak cells), the final, recovered RBCs may be stored at 4° C. for approximately two (2) weeks before being utilized. This extended storage time far exceeds the storage times available with the prior art devices, which are typically limited to twenty-four hours.

It should be understood that the cryopreservation and recovery processes described herein may be implemented and performed separately.

The foregoing description has been directed to specific embodiments of this invention. It will be apparent, however, that other variations and modifications may be made to the described embodiments, with the attainment of some or all of their advantages. Therefore, it is the object of the appended claims to cover all such variations and modifications as come within the true spirit and scope of the invention.

What is claimed is:

1. A method for preparing a blood component for cryopreservation by mixing the blood component with a volume of cryopreservation solution that exposes the blood component to a risk of osmolarity shock, the method comprising the steps of:

determining the volume of cryopreservation solution needed to obtain a desired concentration of cryopreservative within the blood component;

providing the volume of cryopreservation solution in a substantially continuous flow to the blood component at an adjustable flow rate; and dynamically adjusting the flow rate of the cryopreservation solution to the blood component to reduce the risk of osmolarity shock to the blood component.

2. The method of claim 1, wherein the blood component has an osmolarity and wherein the step of dynamically adjusting the flow rate includes adjusting the flow rate to cause the osmolarity of the blood component to increase at a constant rate over time.

3. The method of claim 2, wherein the step of providing is by the means of at least one variable-speed pump such that operation of the pump at a given speed defines a respective flow rate of cryopreservation solution to the blood component, and wherein the step of dynamically adjusting includes periodically changing the speed of the at least one pump.

4. The method of claim 3 wherein the step of dynamically adjusting comprises the step of changing the speed of the at least one pump so that the flow rate of cryopreservation solution is substantially given by the following equation:

$$K[V_i*(W*Hct_i/100)+V_g]^2/[V*(W*Hct_i/100)*(O_i-O_g)]$$

where,

K is the selected rate of increase in osmolarity of the red blood cells, $V_i$ is the volume of red blood cells, W is the volumetric percentage of water in the red blood cells, $Hct_i$ is the hematocrit level of the red blood cells before cryopreservation, $V_g$ is the volume of cryopreservation solution that has already been added to the red blood cells prior to the current flow rate calculation, $O_i$ is the osmolarity of the red blood cells before cryopreservation, and $O_g$ is the osmolarity of the cryopreservation solution.

5. The method of claim 4 further comprising the step of agitating the blood component as the cryopreservation solution is being delivered thereto.

6. The method of claim 4 further comprising the step of adjusting, at least initially, the speed of the at least one pump so that the initial flow rate of cryopreservation solution is substantially given by the following equation:

$$i\ K*V_i*(W*Hct_i/100/(O_i-O_g).$$

7. The method of claim 4 further comprising the step of determining the volume of red blood cells, $V_i$, substantially in accordance with the following equation:

$$NW_i/[1.1*Hct_i/100+1.026*(1-Hct_i/100)]$$

where, $NW_i$ is the net weight of the red blood cells prior to cryopreservation.

8. The method of claim 1 further comprising the step of passing the cryopreservation solution through an anti-bacterial filter.

9. The method of claim 8 wherein the cryopreservation solution has a pressure and the anti-bacterial filter has an operating pressure range, and the method further comprises the step of preventing the pressure of the cryopreservation solution from exceeding the operating range of the anti-bacterial filter.

10. A method for diluting a thawed, cryopreserved blood component with a volume of a dilution solution that exposes the blood component to a risk of osmolarity shock, in preparation for recovery of the blood component, the method comprising the steps of:

providing the volume of dilution solution in a substantially continuous flow to the thawed blood component at an adjustable flow rate;

dynamically adjusting the flow rate of the dilution solution to the thawed blood component, to reduce the risk of osmolarity shock to the thawed blood component.

11. The method of claim 10, wherein the blood component has an osmolarity and wherein the step of dynamically adjusting the flow rate includes adjusting the flow rate to cause the osmolarity of the blood component to decrease at a constant rate over time.

12. The method of claim 11, wherein the step of providing is by the means of at least one variable-speed pump such that operation of the pump at a given speed defines a respective flow rate of cryopreservation solution to the blood component, and wherein the step of dynamically adjusting includes periodically changing the speed of the at least one pump.

13. The method of claim 12 further comprising the step of diluting the thawed blood component with a volume of a hypertonic solution prior to delivering the dilution solution, the hypertonic solution having an osmolarity that is substantially similar to the osmolarity of the blood component.

14. The method of claim 13 wherein the blood component is red blood cells and the step of dynamically adjusting comprises the step of changing the speed of the at least one pump so that the flow rate of dilution solution is substantially given by the following equation:

$$K_D[V_i*(W*Hct_i/100+V_s]^2/[V_i*(W*Hct_i/100)*(O_i-O_s)$$

where, $K_D$ is the desired osmolarity rate decrease, $V_i$ is the volume of the thawed red blood cells after dilution with the hypertonic solution, W is the volumetric percentage of water in the red blood cells, $Hct_i$ is the hematocrit level of the thawed red blood cells after dilution with the hypertonic solution, $V_s$ is the volume of the dilution solution that has already been delivered to the thawed red blood cells, $O_i$ is the osmolarity of the thawed red blood cells after dilution with the hypertonic solution, and $O_s$ is the osmolarity of the washing solution.

15. The method of claim 14 wherein the step of dynamically adjusting further comprises initially adjusting the speed of the at least one pump so that the initial flow rate of dilution solution is substantially given by the following equation:

$$K_D*V_i*(W*Hct_i/100)/(O_i-O_s).$$

16. The method of claim 15 further comprising the step of agitating the thawed blood component as the dilution solution is being delivered thereto.

17. The method of claim 14, wherein the dilution solution comprises a washing solution.

18. A method for preparing biological cells for cryopreservation by mixing the biological cells with a volume of cryopreservation solution that exposes the biological cells to a risk of osmolarity shock, the method comprising the steps of:

determining the volume of cryopreservation solution needed to obtain a desired concentration of cryopreservative within the biological cells;

supplying the volume of cryopreservation solution to the biological cells at an adjustable flow rate;

periodically determining a determined volume of cryopreservation solution already supplied to the biological cells; and adjusting the flow rate of the cryopreservation solution as a function of the determined volume of cryopreservation solution already supplied.

19. The method of claim 18, wherein the flow rate of cryopreservation solution is increased as the determined volume.

20. The method of claim 19, wherein the biological cells are red blood cells and wherein the adjusted flow rate is substantially given by the following equation $$K[V_i*(W*Hct_i/100+V_s]^2/[V_i*(W*Hct_i/100)*(O_i-O_g)$$

where,

K is the selected rate of increase in osmolarity of the red blood cells, $V_i$ is the volume of red blood cells, W is the volumetric percentage of water in the red blood cells, $Hct_i$ is the hematocrit level of the red blood cells before cryopreservation, $V_g$ is the volume of cryopreservation solution that has already been added to the red blood cells prior to the current flow rate calculation, $O_i$ is the osmolarity of the red blood cells before cryopreservation, and $O_g$ is the osmolarity of the cryopreservation solution.

21. A method for diluting thawed, cryopreserved biological cells with a volume of a dilution solution that exposes the biological cells to a risk of osmolarity shock, in preparation for recovery of the biological cells, the method comprising the steps of:

supplying the volume of dilution solution in a substantially continuous flow to the thawed biological cells at an adjustable flow rate;

periodically determining a determined volume of dilution solution already supplied to the biological cells; and adjusting the flow rate of the dilution solution to the thawed biological cells as a function of the determined volume.

22. The method of claim 21, wherein the flow rate of the dilution solution is increased as the determined volume increases.

23. The method of claim 22 further comprising the step of diluting the thawed biological cells with a volume of a hypertonic solution prior to supplying the dilution solution to the thawed biological cells, the hypertonic solution having an osmolarity that is substantially similar to the osmolarity of the biological cells.

24. The method of claim 23 wherein the biological cells are red blood cells and the adjusted flow rate of dilution solution is substantially given by the following equation:

$$K_D[V_i*(W*Hct_i/100+V_s]^2/[V_i*Hct_i/100)*(O_i-O_s)$$

where, $K_D$ is the desired osmolarity rate decrease, $V_i$ is the volume of the thawed red blood cells after dilution with the hypertonic solution, W is the volumetric percentage of water in the red blood cells, $Hct_i$ is the hematocrit level of the thawed red blood cells after dilution with the hypertonic solution, $V_s$ is the volume of the dilution solution that has already been delivered to the thawed red blood cells, $O_i$ is the osmolarity of the thawed red blood cells after dilution with the hypertonic solution, and $O_s$ is the osmolarity of the washing solution.

* * * * *